(12) United States Patent
Kettunen et al.

(10) Patent No.: US 9,040,766 B2
(45) Date of Patent: May 26, 2015

(54) METHOD FOR THE MANUFACTURE OF BRANCHED SATURATED HYDROCARBONS

(75) Inventors: Mika Kettunen, Helsinki (FI); Vaino Sippola, Espoo (FI); Marja Tiitta, Porvoo (FI)

(73) Assignee: NESTE OIL OYJ, Espoo (FI)

( * ) Notice: Subject to any disclaimer, the term of this patent is extended or adjusted under 35 U.S.C. 154(b) by 687 days.

(21) Appl. No.: 12/782,498

(22) Filed: May 18, 2010

(65) Prior Publication Data

US 2010/0298616 A1    Nov. 25, 2010

(30) Foreign Application Priority Data

May 19, 2009    (EP) .................................... 09160616

(51) Int. Cl.
*C07C 5/13* (2006.01)
*C07C 5/22* (2006.01)
(Continued)

(52) U.S. Cl.
CPC ................. *C07C 5/03* (2013.01); *B01J 29/005* (2013.01); *B01J 29/0308* (2013.01); *B01J 29/064* (2013.01); *B01J 29/068* (2013.01); *B01J 29/70* (2013.01); *B01J 29/85* (2013.01); *B01J 2229/20* (2013.01); *B01J 2229/42* (2013.01); *B01J 2229/62* (2013.01); *C07C 5/2775* (2013.01); *C07C 9/22* (2013.01); *C10G 45/62* (2013.01); *C10G 45/64* (2013.01); *C10L 1/08* (2013.01); *C10G 3/45* (2013.01); *C10G 3/47* (2013.01); *C10G 3/49* (2013.01); *C10G 3/50* (2013.01); *C10G 2300/1014* (2013.01); *C10G 2300/1018* (2013.01); *C10G 2300/4006* (2013.01); *C10G 2300/4012* (2013.01); *C10G 2400/04* (2013.01); *C10G 2400/08* (2013.01)

(58) Field of Classification Search
CPC .............. C07C 5/03; C07C 5/13; C07C 9/16; C07C 9/22
USPC ......... 585/250, 251, 253, 275, 277, 700, 734, 585/739
See application file for complete search history.

(56) References Cited

U.S. PATENT DOCUMENTS 3,542,671 A * 11/1970 Pollitzer ........................ 208/136
3,723,552 A *  3/1973 Mitsche et al. ............... 585/481
(Continued)

FOREIGN PATENT DOCUMENTS

WO    WO-2005/012459 A1    2/2005

OTHER PUBLICATIONS

Database of Zeolite Structures, available on-line at www.iza-structure.org/databases, accessed Jun. 25, 2012.*

(Continued)

*Primary Examiner* — Thuan D Dang
(74) *Attorney, Agent, or Firm* — Birch, Stewart, Kolasch & Birch, LLP

(57) ABSTRACT

The invention relates to a method for the manufacture of branched saturated hydrocarbons, said method comprising the steps where a feed comprising olefins having at least 10 carbons is simultaneously hydrogenated and isomerized in the presence of hydrogen at a temperature of 100-400° C., under hydrogen partial pressure of 0.01-10 MPa, in the presence of a catalyst comprising a metal selected from the metals of Group VIIIb of the Periodic Table of Elements, a molecular sieve selected from ten member ring molecular sieves, twelve member ring molecular sieves and mesoporous molecular sieves embedded with zeolite, and a carrier, to yield branched saturated hydrocarbons.

17 Claims, 2 Drawing Sheets

Figure 1:
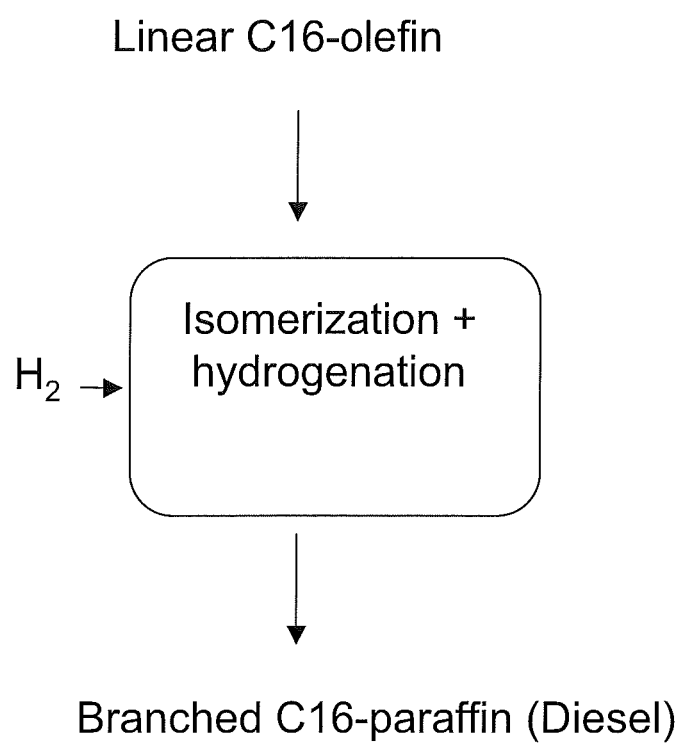

(51) Int. Cl.
  *C07C 5/03*    (2006.01)
  *B01J 29/00*   (2006.01)
  *B01J 29/064*  (2006.01)
  *B01J 29/068*  (2006.01)
  *C07C 5/27*    (2006.01)
  *C07C 9/22*    (2006.01)
  *C10G 45/62*   (2006.01)
  *C10G 45/64*   (2006.01)
  *C10L 1/08*    (2006.01)
  *C10G 3/00*    (2006.01)
  *B01J 29/03*   (2006.01)
  *B01J 29/70*   (2006.01)
  *B01J 29/85*   (2006.01)

(56) References Cited

U.S. PATENT DOCUMENTS

| | | | | |
|---|---|---|---|---|
| 4,300,009 A | * | 11/1981 | Haag et al. | 585/408 |
| 4,417,089 A | * | 11/1983 | Drake | 585/670 |
| 5,019,661 A | * | 5/1991 | Mole | 585/253 |
| 6,054,415 A | * | 4/2000 | Gee et al. | 507/103 |
| 6,930,217 B2 | * | 8/2005 | Shan et al. | 585/467 |

OTHER PUBLICATIONS

Han, et al., "Fuels, Synthetic, Liquid Fuels" in Kirk-Othmer Encyclopedia of Chemical Technology, John Wiley & Sons, 2001, available on-line Dec. 4, 2000.*

Database of Zeolite Structures—Beta Zeolite, avaiable on-line at www.iza-structure.org/databases, accessed Jan. 4, 2013.*

Speight, "Refinery Processes", pp. 449-450, in Kirk-Othmer Encyclopedia of Chemical Technology, John Wiley & Sons, 1996—month unknown.*

AEL Framework in Database of Zeolite Structures, available on-line at www.iza-structure.org/databases, accessed Jun. 10, 2014.*

* cited by examiner

METHOD FOR THE MANUFACTURE OF BRANCHED SATURATED HYDROCARBONS

This Nonprovisional application claims priority under 35 U.S.C §119(a) on Patent Application No. EP 09160616.0 filed in the European Patent office on May 19, 2009, the entire contents of which are hereby incorporated by reference.

FIELD OF THE INVENTION

The present invention relates to a method for the manufacture of branched saturated hydrocarbons. Particularly the invention relates to simultaneous hydrogenation and isomerization of olefins having at least 10 carbon atoms, yielding branched and saturated hydrocarbons. The invention further relates to the manufacture of fuels and base oils from olefins having at least 10 carbon atoms, by simultaneously hydrogenating the double bonds and isomerizing the hydrocarbons to more branched products.

BACKGROUND OF THE INVENTION

Isomerization processes are commonly used within the petrochemical and petroleum refining industry for converting linear olefins to more valuable branched olefins, which may further be hydrogenated to high-octane paraffins.

U.S. Pat. No. 3,749,752 discloses a gas-phase olefin hydroisomerization process where short C4-C9 olefins, typically obtained as refinery offstreams, are simultaneously hydrogenated and hydroisomerized to branched paraffins having more branched carbon skeleton than the precursor olefin. Said process is carried out in the presence of a catalyst containing a platinum group metal, a rhenium component, alumina and mordenite, at a temperature of 0-500° C. and under a pressure of 0-200 atm.

US 2004/0210098 provides a process where C4-C6 monoolefins and terminal double bonds containing α-olefins are isomerized to the corresponding monoolefins having internal bouble bonds and simultaneously any polyunsaturated olefins present are selectively hydrogenated to monoolefins and isomerized to the corresponding monoolefins having internal bouble bonds, in the presence of at least one added sulfur compound and a catalyst comprising transition group VIII element, such as palladium on a support, such as alumina.

A process for preparing isomerized linear olefins is presented in WO 95/21225, where C12-C24 olefins are skeletally isomerized over a catalyst comprising an intermediate pore size molecular sieve, with or without Group VIII metal under skeletal isomerization conditions without hydrogen to yield olefins particularly suitable as drilling fluids. If desired, the obtained olefins may subsequently be hydrogenated as a second step to yield corresponding paraffins.

Often isomerization of higher olefins is associated with cracking to smaller components and with oligomerization because relatively high reaction temperatures and pressures are needed, typically resulting in the decrease of yields and in the deactivation of the isomerization catalyst. Isomerization catalysts containing mordenite usually lead to cracking to smaller components. Additionally, when the hydrogenation is carried out as another separate process step, separate equipment for the isomerization and hydrogenations steps are required, whereby the lead-time is longer and investment costs higher.

So far there are no commercial methods available where heavier olefins having at least 10 carbon atoms are simultaneously isomerized and hydrogenated. Typically heavier olefins are first hydrogenated to yield paraffins, which are subsequently isomerized. This method requires separate reactors for each step and high isomerization temperatures consuming high amounts of energy.

Based on the above it can be seen that there is an evident need for an improved and simplified method for the manufacture of branched saturated hydrocarbons from heavier olefins having at least 10 carbon atoms, particularly as heavier olefins having at least 10 carbon atoms provide a potential source for alternative starting material for branched saturated hydrocarbons.

OBJECT OF THE INVENTION

An object of the invention is a method for the manufacture of branched saturated hydrocarbons, where olefins having at least 10 carbon atoms are simultaneously hydrogenated and isomerized.

A further object of the invention is a method for the manufacture of branched saturated hydrocarbons suitable as diesel fuel, where olefins having at least 10 carbon atoms are simultaneously hydrogenated and isomerized.

A further object of the invention is a method for the manufacture of branched saturated hydrocarbons suitable as base oil or base oil component, where olefins having at least 10 carbon atoms are simultaneously hydrogenated and isomerized.

A further object of the invention is a method for the manufacture of branched saturated hydrocarbons suitable as a component for aviation fuel, where olefins having at least 10 carbon atoms are simultaneously hydrogenated and isomerized.

Characteristic features of the method according to the invention are provided in the appended claims.

DEFINITIONS

Here hydrocracking is understood as catalytic decomposition of organic hydrocarbon materials in the presence of hydrogen.

Here cracking is understood as catalytic decomposition of organic hydrocarbon materials.

Here hydrogenation means saturation of carbon-carbon double bonds by the means of molecular hydrogen under the influence of a catalyst.

Here isomerization is understood to mean as catalytically converting hydrocarbons to more branched products.

Here n-paraffins mean normal alkanes or linear alkanes containing no side chains.

Here isoparaffins mean alkanes having one or more $C_1$-$C_9$, typically $C_1$-$C_2$ alkyl side chains, typically mono-, di-, tri- or tetramethylalkanes.

Here aviation fuel is understood to mean aviation turbine fuel or jet fuel, suitable for aviation purposes.

Here bio jet fuel means aviation fuel derived from biological starting materials.

Typically aviation fuel comprises $C_8$-$C_{16}$ hydrocarbons, typically the initial boiling point being in the range from 130 to 160° C. and final boiling point in the range from 220 to 300° C.

Here a component for aviation fuel typically comprises $C_{10}$-$C_{16}$ hydrocarbons.

Typical boiling range of diesel fuel is from 160 to 360° C., typically comprising $C_{10}$-$C_{28}$ hydrocarbons.

Boiling temperatures refer to temperatures under normal atmospheric pressures unless otherwise provided.

Base oil or base oil component comprises saturated hydrocarbons typically in the range of C18-C100. Saturated hydrocarbons comprise paraffinic and naphthenic compounds but no aromatics. Base oil or base oil component comprises branched and/or linear paraffinic compounds.

Naphthenic compounds are cyclic saturated hydrocarbons, also known as cycloparaffins. Naphthenic compounds may contain one ring structure (monocycloparaffins) or two rings (dicycloparaffins) or several rings (multicycloparaffins).

Olefins are defined herein as a class of unsaturated aliphatic hydrocarbons having one or more double bonds. These olefins may be straight chain olefins or branched chain olefins. The olefins may be alpha-olefins, internal olefins, vinylidene olefins, or mixtures thereof. Monoolefins contain one double bond. Diolefins contain two double bonds and triolefins contain three double bonds. Olefins may be obtained from any sources, including biological raw materials.

In this context, pressures are absolute pressures. Hydrogen partial pressure is the molar ratio of hydrogen to the molar ratio of all components in gas phase. Total pressure is the same or higher than the hydrogen partial pressure.

Classification of the Periodic System of the Elements is the IUPAC classification.

SUMMARY OF THE INVENTION

The present invention relates to a method for the manufacture of branched saturated hydrocarbons, where olefins having at least 10 carbon atoms are simultaneously hydrogenated and isomerized. Branched saturated hydrocarbons, suitable as diesel fuel, base oil or base oil components or components for aviation fuel are obtained. In accordance with the present invention, a new improved method has been discovered for producing branched saturated hydrocarbons from heavier olefins, and particularly from olefins having at least 10 carbon atoms, in the presence of a catalyst comprising a hydrogenation metal, a molecular sieve selected from ten member ring molecular sieves, twelve member ring molecular sieves and mesoporous molecular sieves embedded with zeolite, and a carrier, in the presence of hydrogen, under mild conditions sufficient to effect the desired isomerization and hydrogenation and sufficient to maintain the feedstock and product in liquid form.

The method according to the invention comprises the steps where a feedstock comprising olefins having at least 10 carbon atoms, preferable C10-C100 olefins and particularly preferably C10-C50 olefins are subjected conditions sufficient to effect simultaneously hydrogenation and isomerization to yield isoparaffins having substantially same carbon numbers as the feedstock.

According to one embodiment of the invention, the method utilizes as feedstock olefins having at least 10 carbon atoms, produced from renewable raw materials. Suitably said olefins are obtained from fatty acids originating from renewable sources, such as plant, vegetable, animal and fish fats and oils.

If particularly heavy products, suitable as base oils or base oil components are desired, olefins may be oligomerised to heavier olefins prior to the simultaneous hydrogenation and isomerization.

High quality saturated branched hydrocarbon products olefins having at least 10 carbon atoms are obtained, for example C10-C16 products suitable as components for aviation fuel, C10-C28 products suitable as diesel fuel and C18-C50 products, suitable as base oil or base oil components. If desired, the product is obtainable by employing feedstock of biological origin.

Figure 2:
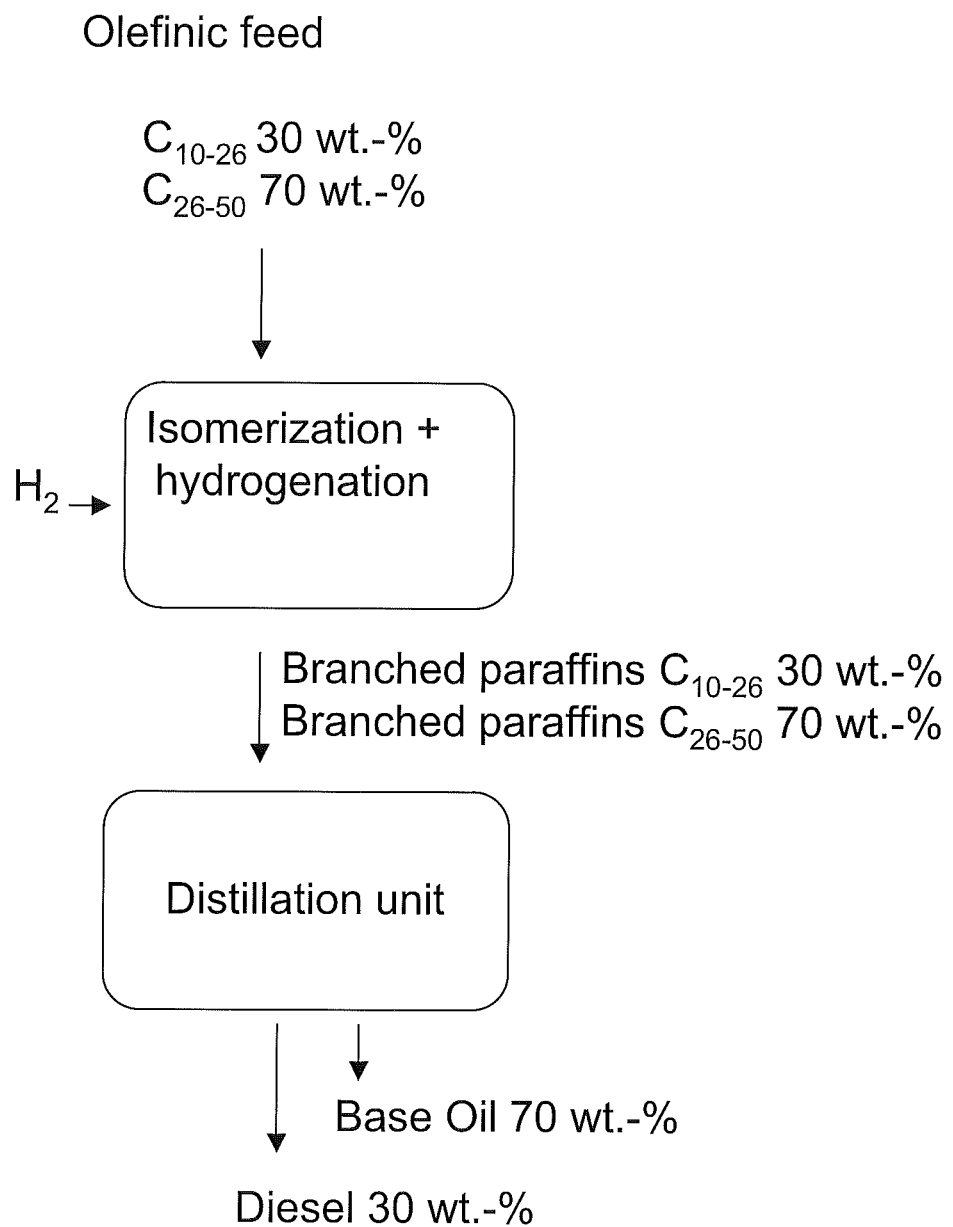

Two embodiments of the method according to the invention are presented in the appended FIGS. 1 and 2.

LIST OF FIGURES

FIG. 1. Manufacture of branched C16 paraffins from liners C16 olefins.

FIG. 2. Manufacture of a base oil and diesel fuel from C10-C50 olefinic feed

In FIG. 1 a schematic presentation is provided describing the method according to the invention where a liquid feedstock comprising linear C16 olefins is subjected to simultaneous isomerization and hydrogenation in the presence of hydrogen to yield branched C16 paraffins suitable as diesel fuel or a component for diesel fuel.

In FIG. 2 another schematic presentation is provided describing the method according to the invention where a liquid feedstock containing 30 wt % of $C_{10-26}$ olefins and 70 wt % of $C_{26-50}$ olefins is subjected to simultaneous isomerization and hydrogenation in the presence of hydrogen to yield 30 wt % of branched $C_{10-26}$ paraffins suitable as diesel fuel or a component for diesel fuel and 70 wt % of branched $C_{26-50}$ paraffins suitable as base oil or base oil component. Suitably these components are separated from the reaction product in a distillation unit.

DETAILED DESCRIPTION OF THE INVENTION

It was surprisingly found that high quality saturated and branched hydrocarbons, suitable as diesel fuel, base oil or base oil component or component for aviation fuel can be obtained from feedstock comprising olefins having at least 10 carbon atoms by simultaneous hydrogenation and isomerization of olefins. Said isomerization is suitably skeletal isomerization of olefins.

Feedstock

The feedstock comprises olefins having at least 10 carbons atoms. Preferable C10-C100 olefins and particularly preferably C10-C50 olefins are used as feedstock. Said olefins may be straight chain olefins or branched chain olefins or combinations thereof. The olefins may be alpha-olefins, internal olefins, vinylidene olefins, or mixtures thereof. Preferably, the olefins are monoolefins. The olefins may be obtained using any method known in the art for the manufacture of olefins.

The olefins may also be obtained from biological raw materials, whereby products originating from renewable sources are obtained. Said biological raw material, such as plant oils and fats, vegetable oils and fats, animal and fish oils and fats, are subjected to structural reformation to yield olefinic compounds, optionally followed by oligomerization to heavier olefins.

In the following some examples of suitable methods for the manufacture of olefins, useful as the feedstock, are described. However, olefins used as feedstock in the method of the present invention are not limited to these examples.

Polyalpha-olefins may be obtained by synthesizing over homogeneous Friedel-Crafts catalyst, such as $BF_3$ or $AlCl_3$, followed by hydrogenation to stabilize the oligomer against oxidation and degradation. In a typical polyalpha-olefin production process, 1-decene is used as the starting material to yield polymers of 1-decene and mixtures of 1-decene with 1-octene and/or 1-dodecene.

Olefins having up to about 20 carbon atoms are prepared by a number of methods including thermal and catalytic cracking of petroleum fractions, thermal cracking of paraffin wax, dehydrochlorination of monochlorinated paraffinic hydrocarbons, polymerization of low molecular weight olefins by the Ziegler process, hydrogenation of fatty acids to alcohols with subsequent dehydration of alcohols to olefins, and hydrogenation of fatty acid esters or triglycerides to paraffins with subsequent dehydrogenation of paraffins to olefins. Fatty alcohols can be produced on commercial scale by hydrogenation of fatty esters, fatty acids or triglycerides.

Dehydration of alcohols to form olefins is one of the oldest catalytic reactions, and numerous oxides are suitable catalysts for this reaction. WO 01/44145 describes a dehydration process to convert C4-C40 alcohols to olefins by a zirconium oxide on aluminium oxide catalyst.

U.S. Pat. No. 4,554,397 discloses a process for the manufacture of linear olefins from saturated fatty acids or esters by decarboxylation, using a catalytic system consisting of nickel and at least one metal selected from the group consisting of lead, tin and germanium. This reaction is applicable particularly to saturated linear carboxylic acids having from 6 to 30 carbon atoms, as well as to esters formed from said acids and mono- or polyhydric alcohol.

U.S. Pat. No. 5,597,944 discloses a process for producing n-olefins via dehydrogenation of C5 to about C20 n-paraffins by dehydrogenating in the presence of manganese oxide octahedral molecular sieve as catalyst.

There are several oligomerization and polymerizations methods available in the art for the manufacture of higher olefins from lower olefins in the presence of various catalysts. A conventional route for preparing 1-decene and other linear alpha-olefins is via oligomerization of ethylene using an alkylated metal catalyst, also resulting in a wide spectrum of products having even-numbered carbon chain lengths. Polymerization of ethylene usually produces a wide range of alpha-olefins, from 1-butene to 1-C20 and higher alpha-olefins, with the product distribution governed by the degree of polymerization.

FI 20065404 provides a process for producing polyalpha-olefins originating from olefins obtained from higher fatty acids. The feedstock is converted to olefins by decarboxylation, or hydrogenated to paraffins with subsequent dehydrogenation of the paraffin to the olefin. In the first step feedstock comprising fatty acids is esterified with at least one fatty alcohol or methanol, in the second step the obtained esters are hydrogenated to fatty alcohols, in the third step the fatty alcohols in turn are dehydrated to alpha-olefins, in the fourth step the obtained alpha-olefins are oligomerized to branched hydrocarbons by contacting them either with a homogeneous or heterogeneous oligomerization catalyst, and in the fifth step the oligomers produced are hydrogenated to produce polyalpha-olefins.

Method

The method according to the present invention comprises the steps where a feedstock comprising olefins having at least 10 carbon atoms is hydrogenated and isomerized simultaneously in the presence of hydrogen at a temperature of 100-400° C., preferably 100-250° C. and particularly preferably 120-200° C. The method is carried out under hydrogen partial pressure of 0.01-10 MPa, preferably 0.01-5 MPa, particularly preferably 0.1-5 MPa. Said method is carried out under the total pressure of 0.1-15 MPa, preferably 0.2-10 MPa. Said isomerization is suitably skeletal isomerization of olefins.

The simultaneous hydrogenation and isomerization is performed in the presence of a catalyst comprising a hydrogenation metal selected from metals of Group VIIIb of the Periodic Table of Elements, a molecular sieve selected from ten member ring molecular sieves, twelve member ring molecular sieves and mesoporous molecular sieves embedded with zeolite, and a carrier.

Preferably the metal is platinum, palladium, nickel, cobalt or iridium, particularly preferably platinum or nickel.

Preferably the molecular sieve selected from ten member ring molecular sieves and twelve member ring molecular sieves is SAPO-11, ZSM-23, ZSM-22, beta or ZSM-12, particularly preferably SAPO-11.

The mesoporous molecular sieve embedded with zeolite is a solid acid catalyst having mesoporous surface area more than 600 $m^2/g$, determined by nitrogen absorption technique and calculated from the BHJ-equation. Said solid catalyst material is crystalline (not amorphous) and it contains crystalline zeolite phases, where the zeolite phase is selected from MTT, TON, MTW and BEA framework type zeolites. Said catalyst material contains only silicon, aluminum and oxygen. Further, the catalyst material comprises at least 100 μmol/g acid sites measured by $NH_3$-adsorption technique and it comprises at least 50 μmol/g Bronsted acid sites measured by H-NMR technique.

The catalyst comprises a carrier, which is preferably selected from clay, alumina, silica and zirconia, particularly preferably it is alumina.

The method according to the invention is carried out under conditions sufficient to maintain the feedstock and products in liquid form.

An inert protection gas may optionally be used.

The method according to the invention may be carried out in a reaction zone comprising any type of reactor suitable for liquid phase operation and in which a solid catalyst can be used. Typically these reactor types include fixed bed reactors, moving bed reactors, mixing tank reactors, fluidized bed reactors, spouted bed reactors and any combinations thereof. The weight hourly space velocity (WHSV) is suitably 0.1-100 of weight g of feed per h/g of catalyst ($h^{-1}$), preferably WHSV being 1-50 $h^{-1}$.

There may also occur a need for occasional regeneration of the catalyst, which may conveniently be carried out in facilities for catalyst regeneration, which complement the reactor zone used in the method. If desired, the operation may be interrupted for catalyst regeneration, however in continuous industrial operation it is preferred to include several reactors in the system and carry out regeneration in one reactor at a time while allowing production in other reactors. As an example of such arrangement, two or more fixed bed reactors connected in such manner that each of them can be separated from the process for changing or regeneration of the catalyst can be mentioned.

Alternatively a reactor from which the catalyst can be extracted continuously for regeneration may be used. For this purpose, a fluidized bed reactor or a spouted bed reactor is suitably used, from which the catalyst can be extracted continuously and recycled through a regeneration facility.

The product, which is a mixture of saturated branched hydrocarbons, is fractionated suitably by distillation into desired fractions, such as diesel fuel, aviation fuel component and base oil fractions.

When a feedstock having a narrow carbon number range is used, for example a feedstock containing predominantly only C16 or C18 olefins, also a product having the corresponding carbon number range is obtained.

The method according to the invention provides a product comprising saturated branched hydrocarbons having at least 10 carbons atoms, preferably C10-C100 hydrocarbons. Particularly fractions comprising C10-C16 hydrocarbons, suitable as components for aviation fuels, C10-C28 hydrocarbons, suitable as diesel fuels and C18-C050 hydrocarbons, suitable as base oils or base oil components are obtained.

In addition, some monocycloparaffinic structures may be formed, which provide improved solubility for optional additives in the products.

The component for aviation fuel fraction comprises C10-C16 hydrocarbons. It may be blended with aviation fuels or other aviation fuel fractions to provide fuel products suitable for aircrafts.

The diesel fuel fraction comprising C10-C28 hydrocarbons may be used as such or blended with other diesel components.

The base oil fraction comprises typically C18-C50 hydrocarbons. It has a pour point below −15° C. The viscosity index of the product is typically higher than 120. It may be used as such or blended with other base oil components.

Also heavier products with high viscosity may be obtained and they may be used in industrial oils as well as engine oils.

The hydrocarbon product obtained with the method according to the invention and manufactured from renewable sources contains $^{14}C$-isotope, which can be used as an evidence of the bio origin of the product. The typical $^{14}C$ content of the branched, saturated hydrocarbon product manufactured from feedstock originating from renewable sources is 100%, based on radio-carbon content compared to radio-carbon content of air in the year 1950.

By careful selection of the starting material, reaction conditions, and catalysts, the properties of the products may be controlled. The molecular weight and branching of the olefins has influence on the kinematic viscosity of the products.

Advantages

The method according to the invention has several advantages. The selectivity of this one-step method is very good. Particularly a feedstock containing a narrow carbon number range provides a product with similar narrow carbon number range.

Suitably moderate reaction conditions can be used, resulting in decreased energy consumption. Typically the catalyst is deactivated slowly and undesired cracking and olimerization takes place to a negligible extent only. No additional chemicals such as sulfur or halogen compounds are needed in the method.

With the method according to the invention a branched, saturated hydrocarbon product suitable as a component for aviation fuel, as diesel fuel and as base oil or base oil component is obtained. Said product may also be obtained from renewable sources, which can be determined from its $^{14}C$ isotope content. Such products originating from biological material have significant environmental benefits in terms of decreased global warming impacts, reduced emissions, and a positive impact on agriculture.

Branching in the paraffinic carbon chain enhances low temperature properties, such as pour point, cold filter plugging point and viscometric properties under low temperature and high shear, said properties being particularly useful for diesel fuels and base oils. The good low temperature properties make it possible to use the branched, saturated hydrocarbon products also in the arctic environment.

The following examples illustrate the method according to the present invention with some preferable embodiments and provide physical properties of typical products. However, it is evident to a person skilled in the art that the scope of the invention is not meant to be limited to these examples only.

EXAMPLES

Catalysts A, B and C were used in the examples. Catalyst A was a commercial hydrogenation catalyst containing Ni on alumina (catalyst used in comparative examples), Catalyst B was a mesoporous molecular sieve embedded with zeolite, and Catalyst C was a catalyst containing platinum, SAPO-11 and alumina. The preparation of catalyst B is described in example 1.

Example 1

Preparation of Catalyst Suitable for Simultaneous Hydrogenation and Isomerization of Olefinic Starting Material Synthesis of Pt/ZSM-23 embedded on MCM-41/alumina (Catalyst B)

Firstly, MIT-framework zeolite nucleis were prepared in following manner:

8.80 g of sodium hydroxide was added to 391 g of distilled water and stirred for 20 min (Solution A). 33.00 g of fumed silica was added to Solution A slowly during a period of 30 min. After addition of all of fumed silica it was further stirred for 20 min (Solution B). 3.00 g of aluminium sulphate was added to 49.00 g of distilled water. 17.00 g of pyrrolidine was added slowly over a period of 15 minutes and stirred for 10 min. After addition of all of template (pyrrolidine), the mixture was stirred for 70 minutes (Solution C). Solution C is slowly added to the Solution B. Then, 7.80 g of sulphuric acid was added slowly. The synthesis was carried out in rotation mode at 180° C. for 40 h. After completion of the synthesis autoclaves were quenched, and the product was mixed with distilled water, and then filtered and washed with distilled water. The sample was then dried at 110° C. for 12 h. The removal of template was carried out at 500° C.

Secondly, these zeolite nucleic were embedded as described below:

The synthesis of Na-MM-MTT-2AI was carried out by preparing of solutions A, B and C. Solution A was prepared by mixing 8.30 g of fumed silica (Aldrich) with 51.7 g distilled water with continuous stirring. Solution B was prepared by adding 18.10 g of tetramethylammonium silicate (Aldrich) to 11.70 g sodium silicate (Merck). Solution C was prepared by dissolving 26.30 g of tetradecyltrimethylammonium bromide (Fluka) in 174.3 g distilled water with vigorous stirring. Solution B was added to Solution A slowly with vigorous stirring, after addition of all of solution B the mixture was stirred for further 20 min Solution C was added to Solutions A+B slowly with vigorous stirring after addition of all of solution C, it was further stirred for 20 minutes. After that 3.80 g of MTT zeolite nuclei precursor was added to the gel solutions (A+B+C) under vigorous stirring. 1.90 g of aluminium isopropoxide (Aldrich) was added to the mixture. After that gel was allowed to ripen for three hours with stirring. After measuring pH (above 9), the gel was introduced in teflon cups which was then inserted in 300 ml autoclaves. The synthesis was carried out for 96 h at 100° C. After completion of the synthesis, the reactor was quenched, and mesoporous material was filtered and washed thoroughly with distilled water. Na-MM-MTT-2Al, as synthesized was dried at 110° C., and calcined at 500° C.

Thirdly, this embedded zeolite was converted to acid form. This was carried out by ammonium ion exchange and calcinations as follows: 10 g Na-MM-MTT-2Al was ion-exchanged with 1 M ammonium nitrate aqueous solution for 24 h at ambient temperature. After the ion-exchange the mesoporous molecular sieve material was washed thoroughly with distilled water, dried at 110° C. for 12 hours, calcined at 500° C. for four hours in a muffle oven using step calcinations procedure.

The obtained proton form of the catalyst material was supported with alumina carrier. This was carried out by using boehmite as source material for alumina, using the method described below:

6.60 g of the above-prepared material (H-MM-MTT-2Al) was mixed with 1.70 g of boehmite (Catapal B). This mixture was peptized with acetic acid, dried at 120° C., and calcined at 500° C. The prepared material was crushed and sieved for a desired grain size.

Finally, the hydrogenating metal was added to the catalyst. In this example the platinum was added by incipient wetness impregnation as follows:

Platinum was added by incipient wetness impregnation method for the catalyst (H-MM-MTT-2Al+alumina). The platinum source was Pt(NH3)4(NO3)2. The pore volume of catalyst was measured by water titration. The platinum source was dissolved to the water content measured. The amount of catalyst material was 5.60 g and the amount of Pt(NH3)4(NO3)2 was 0.06 g. The catalyst was impregnated, dried at 115° C. overnight, and calcined at 350° C. in air for two hours. The rate of temperature increase was 0.2° C./min.

Example 2

Simultaneous Hydrogenation and Isomerization of Olefinic Starting Material

The olefinic starting material was obtained from dimerization of C16-C18 olefins, manufactured from C16-C18 fatty alcohols by dehydration. Said olefinic starting material was used as in the method. The composition of the olefinic starting material is presented in the following Table 1.

TABLE 1

| Composition of the olefinic starting material/GC | | | | | | | |
|---|---|---|---|---|---|---|---|
| Carbon number | <C14 | C14 | C16 | C18 | C19-C31 | Dimers (C32-C36) | Trimers + heavier | Branched C16/ linear C16 |
| GC area-% | 0.4 | 0.1 | 7.5 | 17.2 | 3.0 | 39.4 | 32.4 | 0.9 |

The above starting material/feed was processed in the presence of hydrogen at a temperature of 200° C. and under hydrogen partial pressure of 5.0 MPa in the presence of different catalysts in Parr batch reactor.

Almost complete hydrogenation was achieved with all catalysts as can be seen based on Br index in Table 3. None of the catalyst had any cracking or oligomerizing effect on the feed. Only catalyst C had a significant isomerizing effect as can be seen from the ratio of branched C16 hydrocarbons to linear C16 hydrocarbons. Similar effect could be seen also with C18 hydrocarbons. The increase of branching, caused by isomerization, has a significant effect on the cold flow properties of the product.

The compositions of the products obtained with the tested catalysts are presented in following Table 2. Table 3 presents the properties of the obtained products.

TABLE 2

| Composition of the products/GC | | | | | | | | |
|---|---|---|---|---|---|---|---|---|
| Catalyst | <C14 | C14 | C16 | C18 | C19-C31 | Dimers (C32-C36) | Trimers + heavier | Branched C16/ linear C16 |
| A | 0.4 | 0.3 | 7.4 | 17.5 | 2.8 | 40.5 | 31.1 | 1.3 |
| C | 0.5 | 0.3 | 7.3 | 17.7 | 2.7 | 40.8 | 30.7 | 6.0 |

TABLE 3

| Properties of the products | | | |
|---|---|---|---|
| Catalyst | Br index/mg/100 g | Cloud point/° C. | Pour point/° C. |
| A | 60 | 17.3 | −2.5 |
| C | 30 | −7.0 | −10.9 |

The products, obtained with catalyst A and C were further subjected to fractionation by distillation where a middle distillate fraction suitable as diesel fuel (cutting point 413° C.) and base oil fraction were separated. Properties of these fractions are presented in Table 4. From the results it can be seen that simultaneous hydrogenation and isomerization with catalyst C improves significantly the cold flow properties of the product.

TABLE 4

Properties of separated products

| Catalyst | Boiling range/ fraction | Yield % | Cloud point/ °C. | Pour point/ °C. | Density g/L | Cetane index | Viscocity 100° C. mm²/s | Viscocity index |
|---|---|---|---|---|---|---|---|---|
| A | <413 | 33 | 7.7 | 5.1 | 788.8 | 93.0 | nd | nd |
| A | >413 | 67 | 23.3. | −5.5 | 835.8 | nd | 7.512 | 148 |
| C | <413 | 30 | −10.1 | −12.4 | 785.3 | 98.1 | nd | nd |
| C | >413 | 70 | −5 | −7.7 | 834.4 | nd | 7.490 | 149 | nd = not determined

Example 3

Simultaneous Hydrogenation and Isomerization of Olefinic Starting Material

The olefinic starting material of example 2 was used in this example too. The composition of the starting material is presented in Table 1.

The starting material/feed was processed at a hydrogen pressure of 10 bar (1 Mpa) in the presence of either of catalyst C or catalyst B in Parr batch reactor. Catalyst C was a catalyst containing Pt/SAPO-11/alumina. Catalyst B was Pt/ZSM-23 embedded on MCM-41/alumina catalyst, manufactured as described in example 1.

The starting material was slowly heated from room temperature to 200° C. The first samples were taken at 150° C. and the second samples at 200° C.

From the results shown in Tables 5 and 6, it can be seen that both the isomerization and the hydrogenation with catalyst C proceeded simultaneously without any simultaneous cracking, dimerization or oligomerization reactions. When catalyst B was used, both the isomerization and hydrogenation proceeded simultaneously with only very limited simultaneous conversion in cracking, dimerization and oligomerization reactions.

TABLE 5

Composition of the products/GC

| Catalyst | <C14 | C14 | C16 | C18 | C19-C31 | Dimers (C32-C36) | Trimers + heavier | Branched C16/ linear C16 |
|---|---|---|---|---|---|---|---|---|
| C at 150° C. | 0.4 | 0.3 | 7.3 | 17.4 | 2.8 | 40.2 | 31.6 | 1.4 |
| C at 200° C. | 0.5 | 0.3 | 6.6 | 16.0 | 3.0 | 41.2 | 32.3 | 4.3 |
| B at 150° C. | 0.4 | 0.3 | 6.8 | 16.8 | 2.7 | 40.6 | 32.4 | 1.5 |
| B at 200° C. | 1.5 | 0.7 | 5.9 | 13.4 | 4.7 | 35.0 | 38.7 | 4.0 |

TABLE 6

Properties of the products/Br titration.

| Catalyst | Br index/g/100 g |
|---|---|
| C at 150° C. | 19.6 |
| C at 200° C. | 12.9 |
| B at 150° C. | 24.1 |
| B at 200° C. | 14.1 |

The invention claimed is:

1. A method for the manufacture of branched saturated hydrocarbons, said method comprising simultaneously hydrogenating and isomerizing a feed comprising olefins having at least 10 carbons in the presence of hydrogen at a temperature of 100-400° C., under hydrogen partial pressure of 0.01-10 MPa, in the presence of a catalyst comprising a metal selected from the metals of Group VIIIb of the Periodic table of Elements, a molecular sieve selected from ten member ring molecular sieves and mesoporous molecular sieves embedded with zeolite, and a carrier, to yield branched saturated hydrocarbons, wherein during the isomerizing, there is a catalytic conversion of hydrocarbons to more branched products.

2. The method according to claim 1, further comprising separating said saturated hydrocarbons by distillation into fractions.

3. The method according to claim 1 or 2, wherein the hydrogen partial pressure is 0.01-5 MPa.

4. The method according to claim 1, wherein the temperature is 100-250° C.

5. The method according to claim 1, wherein the metal is at least one member selected from the group consisting of platinum, palladium, nickel, cobalt and iridium.

6. The method according to claim 1, wherein the ten member ring molecular sieve is a member selected from SAPO-11, ZSM-23, and ZSM-22.

7. The method according to claim 1, wherein the carrier is selected from clay, alumina, silica and zirconia.

8. The method according to claim 1, wherein the olefins comprise monoolefins.

9. The method according to claim 1, wherein the olefins comprise C10-C100 olefins.

10. The method according to claim 1, wherein the olefins comprise C10-C50 olefins.

11. The method according to claim 1, wherein the olefins originate from biological raw materials.

12. The method according to claim 1, wherein base oil or base oil component is manufactured.

13. The method according to claim 1, wherein diesel fuel is manufactured.

14. The method according to claim 1, wherein component for aviation fuel is manufactured.

15. The method according to claim 1, wherein the zeolite phase of the mesoporous molecular sieve embedded with zeolite is selected from MTT, TON, MTW, and BEA framework type zeolites.

16. The method according to claim 1, wherein the temperature ranges from 120-200° C.

17. The method according to claim 10, wherein the olefins comprise C32-C36 olefins.

* * * * *